US010252043B2

(12) United States Patent
Chettiar et al.

(10) Patent No.: US 10,252,043 B2
(45) Date of Patent: Apr. 9, 2019

(54) VACCINATION DELIVERY SYSTEM AND METHOD

(71) Applicant: Mayo Foundation for Medical Education and Research, Rochester, MN (US)

(72) Inventors: Kylash R. Chettiar, Phoenix, AZ (US); Vinutha Rajesh, Phoenix, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 2 days.

(21) Appl. No.: 15/492,893

(22) Filed: Apr. 20, 2017

(65) Prior Publication Data

US 2017/0304557 A1 Oct. 26, 2017

Related U.S. Application Data

(60) Provisional application No. 62/325,654, filed on Apr. 21, 2016.

(51) Int. Cl.
*A61M 37/00* (2006.01)
*A61M 5/158* (2006.01)
*A61F 13/02* (2006.01)

(52) U.S. Cl.
CPC ........ *A61M 37/0015* (2013.01); *A61M 5/158* (2013.01); *A61F 13/02* (2013.01);
(Continued)

(58) Field of Classification Search
CPC .................... A61M 5/158; A61M 5/46; A61M 2005/1585; A61M 2005/1586; A61M 37/0015; A61M 2037/0023; A61M 2202/30; A61M 2205/50; A61M 2205/581; A61M 2205/587; A61M 2205/59; A61M 2209/088; A61M 5/3287; A61F 13/02

See application file for complete search history.

(56) References Cited

U.S. PATENT DOCUMENTS

RE25,637 E * 9/1964 Kravitz et al. ....... A61B 17/205
604/47
5,848,991 A 12/1998 Gross et al.
(Continued)

OTHER PUBLICATIONS

Emory' [online] "Flu Vaccine Given in Microneedle Skin Patches Proves Effective in Mice," Apr. 28, 2009, Retrieved Apr. 26, 2018, Retrieved from URL: <http://whsc.emory.edu/home/news/releases/2009/04/flu-vaccine-given-in-microneedle-patches.html>, 3 pages.
(Continued)

*Primary Examiner* — Shefali D Patel
(74) *Attorney, Agent, or Firm* — Fish & Richardson P.C.

(57) ABSTRACT

A device can be used for delivering a dose of a vaccine, a medicine, a medication, a drug, or a prescription. For example, this document describes a wearable vaccination device that plays an audible sound or a musical tune for distracting or entertaining a patient while an intradermal vaccine is delivered via the patient's skin. A control portion of the wearable vaccination device includes a processing unit, a rhythm producer that produces audible sounds to distract or entertain the patient, and an injection module that provides an intradermal injection using one or more microneedles.

17 Claims, 8 Drawing Sheets

(52) U.S. Cl.
CPC .......... *A61M 2005/1585* (2013.01); *A61M 2005/1586* (2013.01); *A61M 2037/0023* (2013.01); *A61M 2202/30* (2013.01); *A61M 2205/50* (2013.01); *A61M 2205/502* (2013.01); *A61M 2205/52* (2013.01); *A61M 2205/581* (2013.01); *A61M 2205/584* (2013.01); *A61M 2205/587* (2013.01); *A61M 2205/59* (2013.01); *A61M 2209/088* (2013.01)

(56) References Cited

U.S. PATENT DOCUMENTS

| | | | | |
|---|---|---|---|---|
| 8,945,482 | B2* | 2/2015 | Mitragotri | A61B 10/0045 422/536 |
| 9,609,921 | B1* | 4/2017 | Feinstein | A44C 5/2071 |
| 2012/0130207 | A1* | 5/2012 | O'dea | A61M 37/0015 600/309 |

OTHER PUBLICATIONS

Emory' [online] Toon .J., "Self-administration of flu vaccine with a patch may be feasible, study suggests," Mar. 3, 2014, Retrieved Apr. 26, 2018, Retrieved from URL: <http://www.news.emory.edu/stories/2014/03/self_administration_of_flu_vaccine_patch/index.html >, 2 pages.

YouTube' [online video] "Flu Patch May Replace Painful Flu Shots," Mar. 3, 2014, Retrieved Apr. 26, 2018, Retrieved from URL: <htttps://www.youtube.com/watch?v=X2GXZMgr9Kk>, 2 pages.

YouTube' [online video] "Flu Patch Medical Course," Dec. 18, 2013, Retrieved Apr. 26, 2018, Retrieved from URL: <https://www.youtube.com/watch?v=-MJxdLqFfF4>, 2 pages.

YouTube' [online video] "New flu patch without syringe," Nov. 30, 2010, Retrieved Apr. 26, 2018, Retrieved from URL: <https://www.youtube.com/watch?v=nLbUz0mZ5jE>, 2 pages.

* cited by examiner

VACCINATION DELIVERY SYSTEM AND METHOD

CROSS-REFERENCE TO RELATED APPLICATIONS

This application claims the benefit of U.S. Provisional Application No. 62/325,654, filed Apr. 21, 2016. The disclosure of the prior application is considered part of and is incorporated by reference in the disclosure of this application.

TECHNICAL FIELD

This document relates to devices for delivering a dose of a vaccine, medicine, medication, drug, or prescription. For example, this document relates to a wearable vaccination device that plays an audible sound or musical tune for distracting or entertaining the patient while an intradermal vaccine is delivered via the patient's skin.

BACKGROUND

The Center for Disease Control & Prevention (CDC) recommends thirty vaccination shots for children and youth aged six months to sixteen years. The mere sight of a syringe needle may scare a person, especially a child, before or while receiving a vaccination. A child might need to be held and comforted while being vaccinated. For some children and families, the process may be a nightmare every time a vaccination is due to be delivered at a doctor's office or other location. So called "Needle Nightmare" is a serious problem not only for ages six months to sixteen years but occasionally for the adults too. The process typically is not a joyful one. Children may not be sufficiently distracted or entertained, if at all, during such procedures so that they are not scared of a syringe.

Retail stores, pharmacies, hospital and physician suppliers, and physician offices do not typically carry or use devices that entertain or distract the patient while receiving an injection.

SUMMARY

Embodiments of the device described herein, also referred to herein as "VAC-I-BRACE™," provide a platform that may be used to help remove or alleviate nightmarish vaccination scenarios with typical vaccination devices. The VAC-I-BRACE™ includes a non-allergic bracelet, band, or strap, which may be of various sizes and made of a non-allergic polymer with adjustable width. The VAC-I-BRACE™ also includes a vaccination unit or medicine/drug delivery system located in the center portion of the bracelet, for example, in an enlarged or "dial" portion thereof. The VAC-I-BRACE™ can play various musical tunes, tones, songs, or audible sounds through a speaker(s), and includes flashing LEDs, a start or activate "Press Me" button, and a skin sensor. The vaccination unit includes a micro-needle with a skin auto-piercing technology. The bracelet, band, or strap (hereinafter bracelet) is adjustable, wraps around the patients wrist, arm, or leg (appendage), and is secured by a bracelet lock or clasp mechanism located at ends of the bracelet as well as by non-allergic adhesives located on a lower surface of the center portion of the bracelet in contact with the patient's skin to hold the entire unit in place. A few other small areas of adhesives may also distributed along the inner surface of the bracelet to further help secure the entire bracelet in place firmly. If the system is not adequately secured, the start or activate button cannot be activated. The VAC-I-BRACE™ may be available in various colors and include graphic or other designs thereon. The audible tones and/or musical tunes advantageously distract or entertain the patient prior to the injection being given.

In one aspect, this disclosure is directed to a device for administering a vaccine intradermally. The device includes: (i) a bracelet including a fastener for attaching the bracelet to a patient's appendage; (ii) a vaccination unit attached to the bracelet, the vaccination unit including a microneedle, the vaccination unit including a set of electromagnets having polarity states relative to each other; (iii) an audio unit attached to the bracelet and including at least one microspeaker; and (iv) a button attached to the bracelet for activating electrical signals to play an audible sound through the microspeaker, and after a delay, to change a portion of the relative polarity states of the set of electromagnets to move the microneedle to administer a vaccine intradermally to the patient through the microneedle.

Such a device may optionally include one or more of the following features. The delay may be less than and including one minute. The delay may be up fifteen seconds or less. The vaccine may deliver a medically effective dose through the microneedle. The device may also include an adhesive sterilized bandage or gauze removably affixed to the bracelet for application to the patient's appendage on or over an area of penetration of the microneedle into the patient's skin. The bracelet may comprise a non-allergic bracelet. The set of electromagnets may include four electromagnets. The bracelet is configured to be secured to the patient's appendage by adhesives and an adjustable bracelet lock attached to the bracelet. The bracelet may include one or more colors or graphic designs. The audible sound may include one or more of musical tones, tunes, and songs. The device may reduce the likelihood of needle stick injury. The device may promote patient compliance for receiving vaccines.

In another aspect, this disclosure is directed to a vaccination platform for distracting a patient prior to medicine or drug delivery. The vaccination platform includes a bracelet for attachment to a patient's appendage; a vaccination unit located in a center portion of the bracelet; and non-allergic adhesive located on the bracelet to secure the bracelet to the patient's skin. The vaccination unit includes a control portion including a processing unit; a rhythm producer for producing audible sounds; and an injection module. The injection module includes a set of electromagnets having relative polarity states, a microneedle, and a drug delivery capsule. The microneedle has a proximal end communicating with the drug delivery capsule and a distal end to provide an intradermal vaccination to the patient when a portion of the relative polarity states of the set of electromagnets are activated by the processing unit. The processing unit controls a delay between a start of the audible sounds and when the vaccination occurs.

Such a vaccination platform may optionally include one or more of the following features. The bracelet may also include a light configured to flash to indicate when the vaccination may occur. The vaccination platform may include a plurality of microneedles. The set of electromagnets may include four electromagnets. The vaccination platform may also include an adhesive sterilized bandage or gauze removably affixed to the bracelet for application to the patient's appendage on or over an area of penetration of the microneedle into the patient's skin.

DETAILED DESCRIPTION

Figure 1:
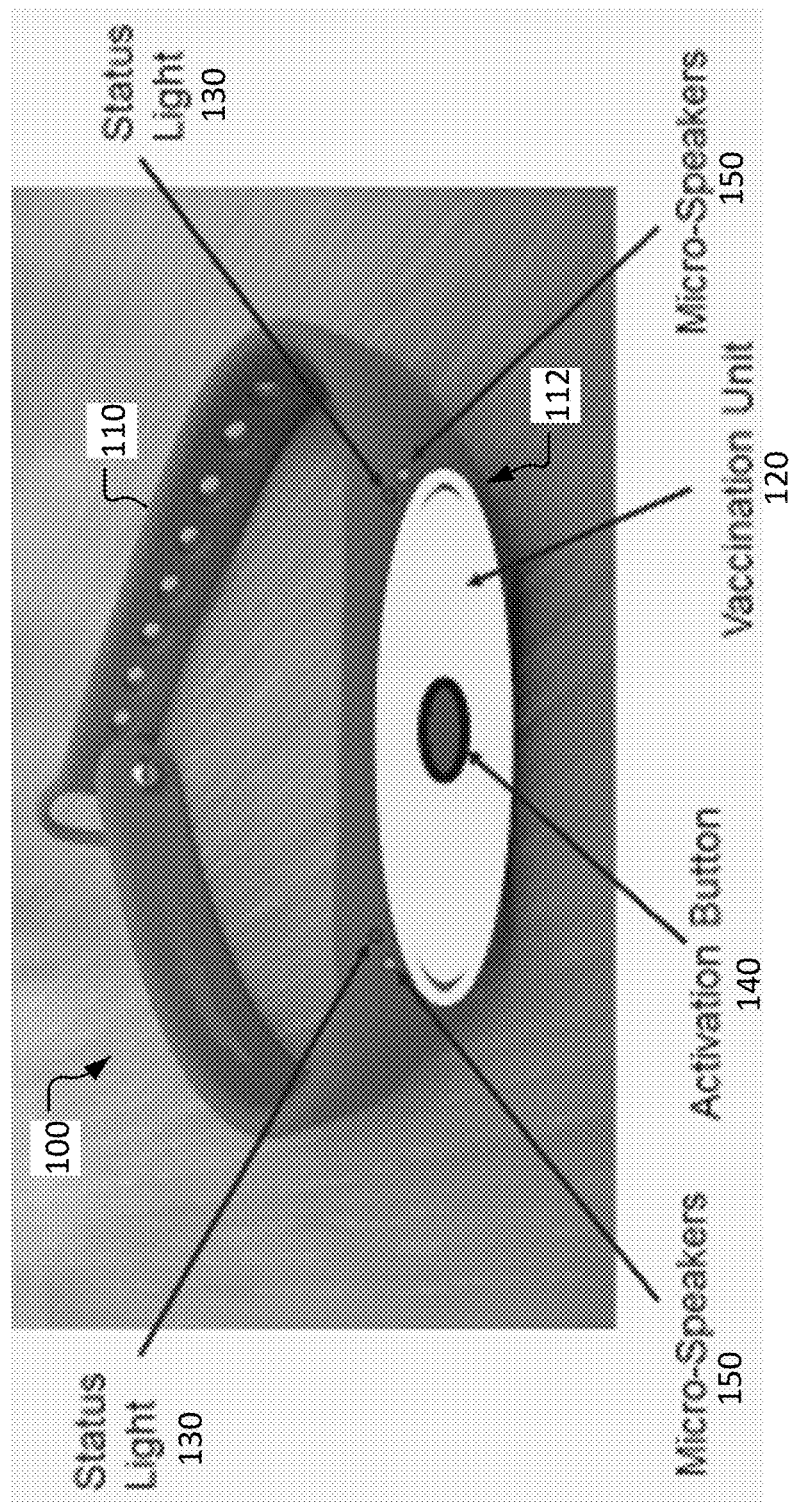
FIG. 1 is a perspective view of an example vaccination platform (VAC-I-BRACE™) showing an adjustable bracelet or strap, a vaccination unit, one or more status lights (e.g., LED(s)), an activation "Press Me" button, and one or more microspeakers in accordance with an embodiment of the invention.
Figure 2:
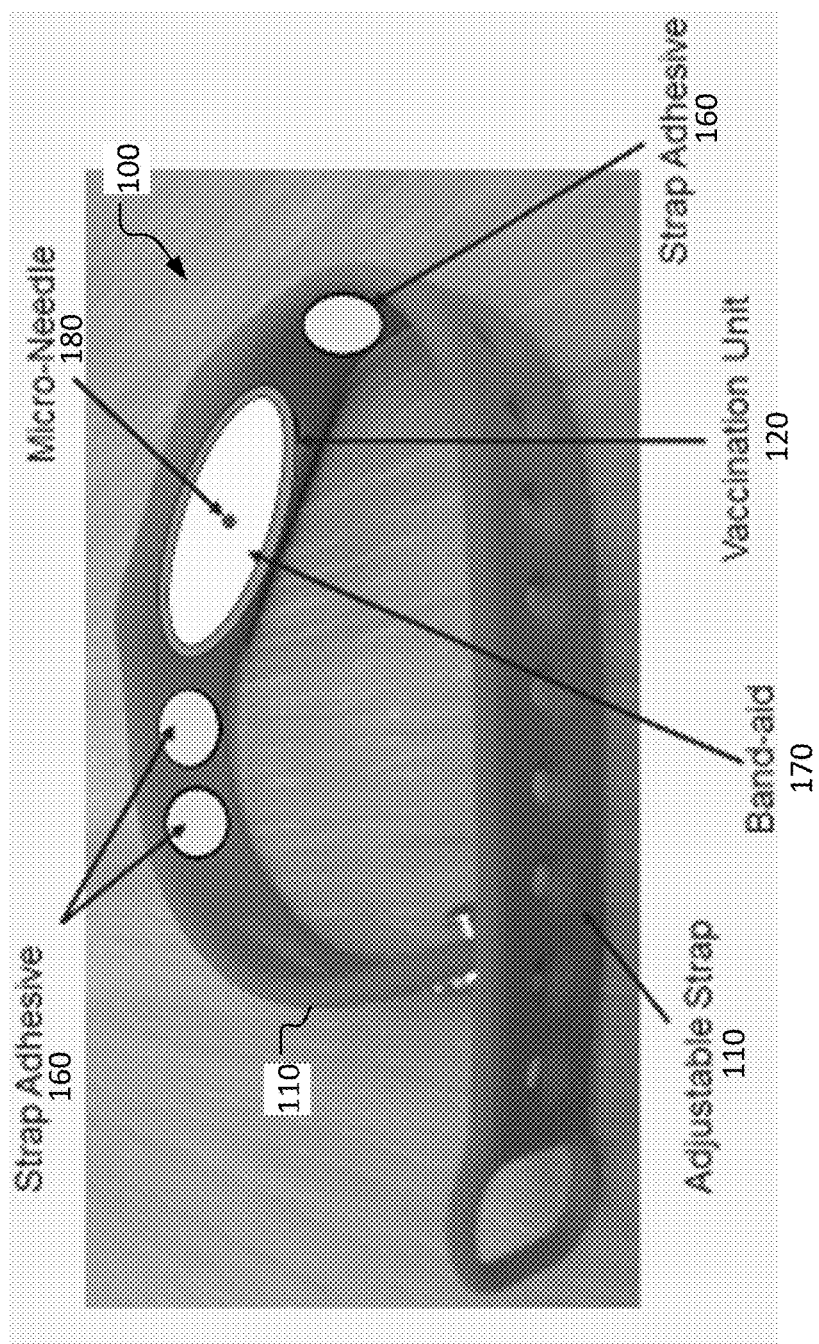
FIG. 2 is another perspective view of the vaccination platform of FIG. 1 showing an adhesive(s), BAND-AID®-like bandage, and the vaccination unit having a microneedle inside.

FIGS. 1 and 2 show views of a vaccination platform 100 (also referred to herein as a VAC-I-BRACE™) showing an adjustable bracelet or strap 110, a vaccination unit 120, one or more status lights 130 (e.g., an LED(s)), an activation "Press Me" button 140, one or more microspeakers 150, one or more adhesive areas 160, a BAND-AID®-like bandage 170, and one or more microneedle(s) 180. It should be understood that some embodiments may not include all of the aforementioned features. For example, in some embodiments no adhesive areas 160 are included.

In accordance with embodiments described herein, the vaccination platform 100, also referred to herein as a VAC-I-BRACEυ, includes a bracelet 110 with a single slotted microneedle 180 enclosed in a small safety unit. In addition to the bracelet 110, the vaccination unit 120 includes three main other portions: a control portion, a rhythm producer, and an injection module. The control portion includes a processing unit, the rhythm producer produces audible sounds to distract or entertain the patient, and the injection module provides an intradermal injection. All three main portions may be located inside a "dial" or expanded portion 112 of the bracelet 110. The injection module may be constructed within a non-allergic, hermetically sealed, and sterilized socket that may be stainless steel or another metal. The rhythm producer produces audible sounds played through a microspeaker(s) 150, which start when the power button 140 is activated. Each vaccination platform 100 can be customized to play a particular musical tone sequence that the subject may choose.

The vaccination platform 100 allows a vaccination to be self-administered by the patient or administered by another person, such as medical doctor, nurse or parent. When the patient or the other person pushes or contacts a "Press Me" button 140, switch, haptic input, or another type of input device such as a touchscreen, an electrical or electronic signal is activated that causes the vaccination platform 100 to play an audible sound or tune for a short period of time, e.g., up to and including one minute. In certain other embodiments, the short period of time may be up to and including fifteen seconds, and in yet other embodiments, up to and including forty-five seconds, although other longer times are contemplated. After a delay, and while the tune is playing, a vaccine dose of a medically effective fluid, medicine, drug, or material is injected into or through the patient's skin (e.g., an intradermal or subcutaneous injection) from a fluid-containing drug delivery capsule or chamber through the micro-needle 180 in physical communication with the fluid-containing chamber in the vaccination unit 120. An adhesive sterilized bandage or gauze, such as a BAND-AID®-like bandage 170, removably affixed beneath the bracelet 110, is applied on or over the area of needle penetration into the patient's skin during or after vaccination to protect the area where the injection is given and after the vaccination platform 100 is removed from the patient.

The bracelet 110 is preferably non-allergenic. A vaccination unit 120 of the vaccination platform 110 includes the fluid-containing chamber or drug delivery capsule that is previously filled through a port (not shown) with the medicine/drug to be injected. The filling method allows the capsule to remain hermetically sealed. The vaccination unit 120 also includes a microneedle(s) 180 with automatic skin-piercing technology, in accordance with some embodiments of the invention described below. Other embodiments include an array of microneedles 180. For example, Emory and Georgia Institute of Technology research related to a so-called "Flu-Patch" uses micro-needle skin patch technology to deliver vaccines, which is incorporated herein by reference. The bracelet 110 is secured to the patient's arm by adhesives 160 and an adjustable mechanism or fastener, strap lock, clip, buckle, clasp, or the like located at ends of the bracelet 110 away from the vaccination unit 120. The bracelet 110 may be provided in various colors, and may include graphic designs and provide musical melodies tones, tunes, songs, audible sounds, etc., as described below. Some implementations of vaccination platform 100 also reduce the likelihood of so-called needle stick injury and may promote patient compliance with being vaccinated because the patient is distracted or entertained during the vaccination.

The vaccination platform 100 also includes or has attached thereto a power unit, such as a battery (not shown) for driving the audio sound. The data for the audio sound may be stored in a UM66 chip. The audio data is converted to audio signals by the rhythm producer that is controlled by the microprocessor. The audio signals are played through the microspeaker(s) 150, which is also included in the vaccination platform 100. A delay timing mechanism is included in the vaccination unit 120 as part of the processing unit as hardware circuitry, or as software code stored in the memory that is executed as instructions in the processing unit, or a combination of both, to delay the time between the onset of the audible sound and when the vaccine actually is administered to the patient.

In some embodiments, the needle 180 preferably is an 18-gauge micro-needle designed to pierce the skin into the dermis layer to deliver the medicine/drug subcutaneously for adequate absorption without any leakage across the needle 180. The tip of the micro-needle 180 is safely secured above the level of a lower surface of the vaccination unit 120 of the vaccination platform 100. The micro-needle 180 is contained and supported within the vaccination unit 120 through a central orifice within a magnet or magnetic component, and is easily able to slide up and down, and the lower surface of the vaccination platform 100 is constructed to present the microneedle(s) 180 at an angle of 15-45 degrees inclusive or approximately (e.g., ±10%) at those range of angles relative to the surface of the patient's skin for skin piercing to facilitate adequate and safe delivery similar to a manual intradermal injection method, as will be appreciated by a person of ordinary skill in the art. A proximal end of the microneedle 180 is directly connected to and physically communicates with the medicine containing unit (drug delivery capsule). "Physically communicates" here means that the proximal end of the microneedle 180 includes a slot 182 into which the medicine/drug will flow from the filled drug delivery capsule. The distal end of the microneedle 180 is safely secured just above the lower contact surface of the vaccination unit 120 inside the injection module prior to and after injection. The distal end of the microneedle 180 is the end which punctures the patient's skin to deliver the medicine/drug intradermally.

Figure 8:
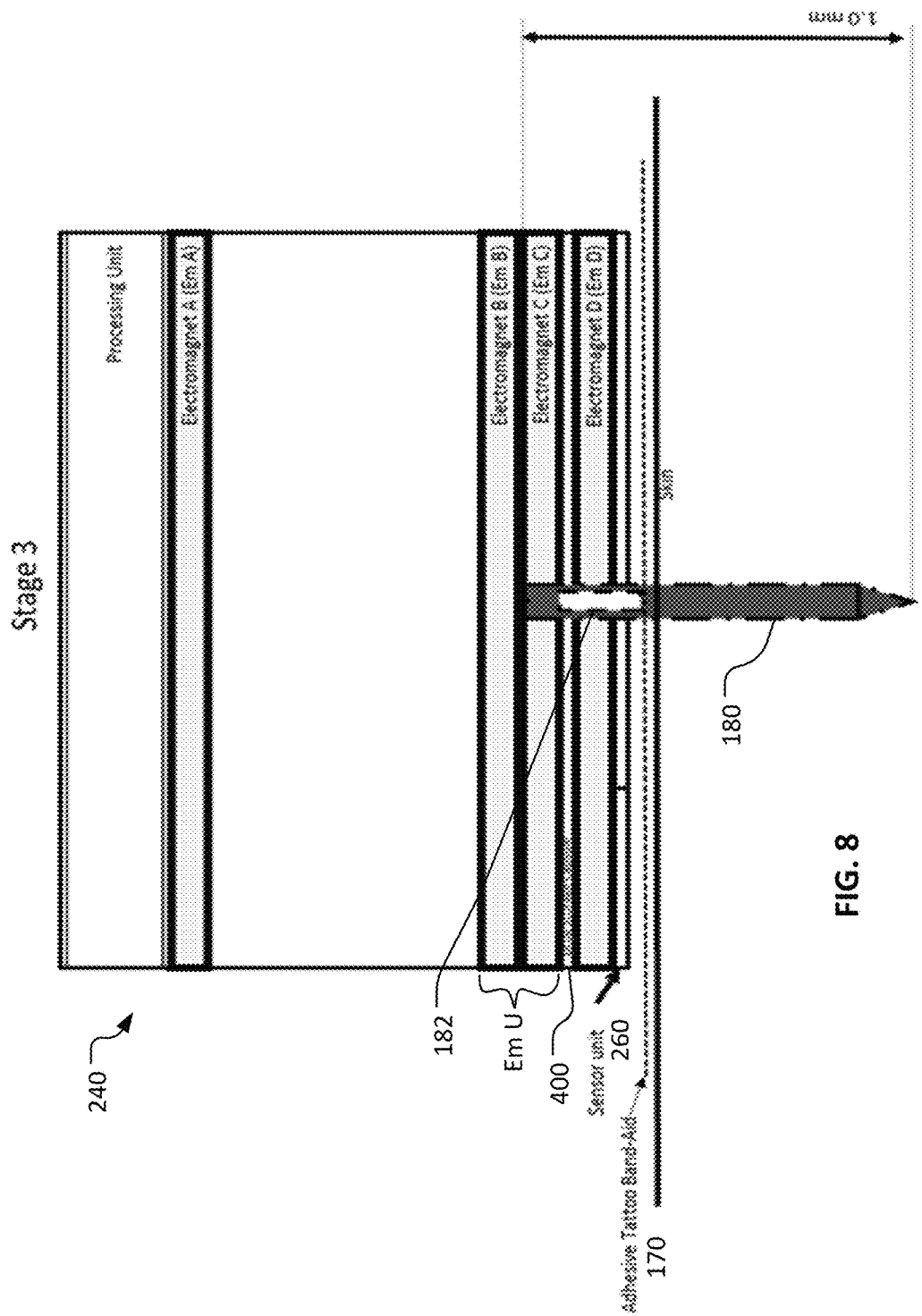
FIG. 8 schematically shows the injection module and electromagnets of FIG. 6 and Stage 3 of the vaccination process in accordance with an embodiment of the invention.

When two electromagnets (e.g., Em U and Em D, as shown in FIG. 8), attract each other after delivering the medicine completely into the patient's skin, as described below, the microprocessor controls a change in their magnetic polarity to make like magnetic poles face each other and therefore repel and move apart, resulting in the retraction of the microneedle(s) 180 from the patient's skin to a safety place or location within the vaccination unit 120. The vaccination unit 120 and the microneedle(s) 180 preferably are designed to allow the microneedle(s) 180 to penetrate from 0.5 to 1.0 mm inclusive (or approximately, e.g., ±10% of those depths) into the patient's skin in accordance with an embodiment of the invention. Other penetration depths are possible in other embodiments. The medicine containing unit also has an aperture (not shown) at a side of the vaccination unit 120 in the event it has to be accessed manually, such as if the microneedle(s) 180 becomes jammed or needs to be replaced. The vaccination unit 120 may be re-sterilized and a new needle(s) 180 inserted in certain embodiments.

Figure 3:
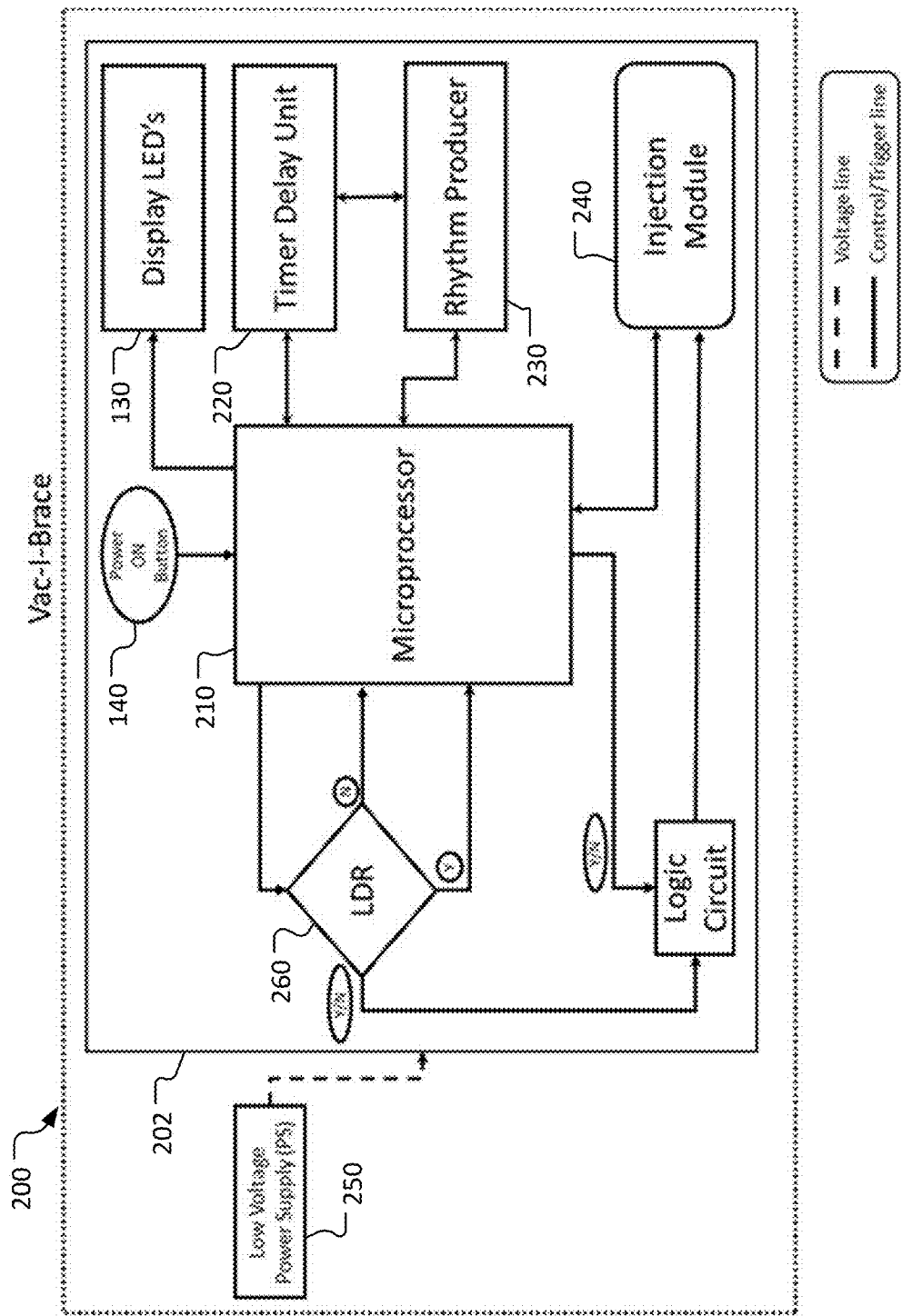
FIG. 3 shows a block diagram of a portion of a vaccination unit that includes a processing unit including a microprocessor, a rhythm producer, a timer delay unit, a logic circuit, a light-dependent resistor (LDR), a display unit (LED(s)), a low voltage power supply, and an injection module, in accordance with an embodiment of the invention.

Referring also to FIG. 3, an example block diagram 200 of a portion of a VAC-I-BRACE™ vaccination unit 120 shown and includes a processing unit 202 having a microprocessor 210, a logic circuit and a timer delay unit 220, and a rhythm producer 230 and an injection module 240. The vaccination unit 120 may be activated by pressing a "Press Me" power on button 140, which initiates a low voltage power supply 250 to trigger the processing unit 202. FIG. 3 illustrates voltage lines (dotted lines) between the power supply 250 and the processor unit 202 and the control lines (solid) between the various components of the vaccination unit 120. The functions of the trigger lines are activating/deactivating the VAC-I-BRACE™, monitoring the rhythm generator clock, sensing the skin contact, sensing the polarity of the electromagnets, and activating the injection module.

In accordance with an embodiment of the invention, the microprocessor 210 used in the vaccination unit may be an 8086-type or 8088-type microprocessor chip or module or similar thereto. The microprocessor 210 activates the timer delay unit 220 in the processing unit 202 and a rhythm producer 230, and waits for a light-dependent resistor (LDR) skin sensor 260 signal to trigger the injection module 240 (or vaccination unit). Activation of the injection module 240 occurs only when the entire VAC-I-BRACE™ 100 is tightly secured or securely fastened with adequate skin contact to the patient. The LDR skin sensor 260 is a safety device or valve, and the microprocessor 210 will only activate the injection module 240 if AND gate-type logic functions are satisfied in the logic circuit. The logic circuit may include a Quad 2 input AND gate 74LS08 chip. The logic circuit truth table is shown in Table I below.

TABLE I

Logic Parameters where value Zero is a 'No' logic and value 1 is a 'Yes' logic

| Microprocessor Output | LDR Output | Logic Circuit Output to Injection Module | Triggering Description |
|---|---|---|---|
| 0 | 0 | 0 | VAC-I-BRACE ™ on Standby |
| 0 | 1 | 0 | LDR sensed skin contact but microprocessor was not ready, malfunction of unit or the skin contact was not sufficient. |
| 1 | 0 | 0 | LDR did not sense skin contact or malfunctioned. Therefore, the injection module is not activated. |
| 1 | 1 | 1 | Unit activated. |

However, if the LDR 260 senses inadequate skin contact, signals are sent to the microprocessor 210, which in turn inhibits the signals to the logic circuit and prevents the activation of the injection module 240. When light detected by the LDR skin sensor 260 is cut off or sufficiently reduced to generate a sensing signal received by the microprocessor 210 because the VAC-I-BRACE™ 100 is properly affixed to the patient, only then will the microprocessor 210 activate the injection module 240 to provide the vaccination. Proper skin contact may be indicated by an LED(s), such as a status LED(s) 130 that lights up or flashes, for example, a green LED, that the patient or person administering the vaccine can see. In other embodiments, other types of sensors may be used instead of or in addition to an LDR 260 to confirm adequate skin contact. These include a capacitive or resistive skin sensor, which in turn may be connected to the LED(s) 130 and the microprocessor 210. The microprocessor 210 then generates the necessary control signals to change the polarity of electromagnets through the low voltage power supply 250 and to trigger the injection module 240 to deliver the medicine/drug, as will be described further below.

The microprocessor 210 will also activate the rhythm producer 230 to produce tones, tunes, music, etc. The rhythm producer 230 includes a melody generator module, a dynamic microspeaker(s) 150, and an LED(s) 130 for a visual display, in accordance with an embodiment of the invention. The LED(s) 130 for the visual display may be a flashing or steady LED(s) 130 and it or other LED(s) 130 included as part of the vaccination unit 120 may indicate status, such as when the unit is turned on, when proper skin affixation has occurred, when the vaccination begins, and when the needle 180 is safely retracted so that the vaccination platform 100 may be removed from the patient.

Figure 4:
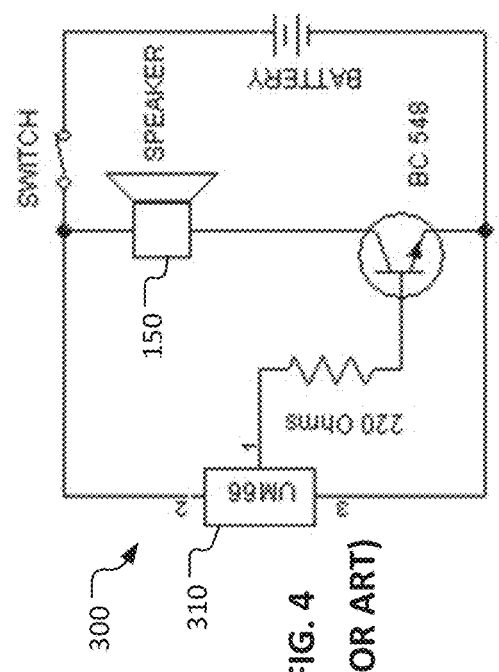
FIG. 4 shows a typical prior art circuit using an UM66T series module for a melody generator.

A typical circuit of an audio unit 300 using a UM66T 310 series module by UMC for the melody generator is shown in FIG. 4, which also shows the microspeaker(s) 150. The UM66T chip 310 is preloaded with melodies or music, some of which are shown in Table A (below). Other melodies and music are contemplated, including simple tones, tunes, and/or popular songs (hereinafter, audible sounds). Patients may choose amongst various bracelet design variations using these or similar chips and having different included audible sounds. For instance, the chip UM66TO1 L/S can play the tunes Jingle bells, Santa Claus Is Coming To Town, and We Wish You A Merry Christmas, as shown in Table A (below).

In accordance of an embodiment of the invention, upon activation of the bracelet 100, the microprocessor 210 is activated by applying power from the power supply 250 and initialized. Then the rhythm producer 230 is activated by applying power from the power supply 250 and controlled by the microprocessor 210. This activation is followed by a delay of less than or equal to 45 seconds (e.g., 10 seconds), and then triggering of the injection module 240 to give the injection. These possible delays are merely exemplary and other delay time lengths are contemplated. The rhythm producer 230 provides the audible sounds to distract or entertain the patient during the entire process, from initiation through vaccination, which may be, for example, for up to 60 seconds inclusive or approximately 60 seconds (e.g., 60±10% seconds). Other process times are contemplated, such as less than or equal to 2 minutes.

TABLE A

UM66T Melodies

| Part No. | Song Name |
| --- | --- |
| UM66T01 L/S | Jingle Bells + Santa Claus is Coming To Town + We Wish You a Merry X'mas |
| UM66T02 L/S | Jingle Bells |
| UM66T04 L/S | Jingle Bells + Rudolph, the Red-nosed Reindeer + Joy to the World |
| UM66T05 L/S | Home Sweet Home |
| UM66T06 L/S | Let Me Call You Sweetheart |
| UM66T08 L/S | Happy Birthday to You |
| UM66T09 L/S | Wedding March (Mendelssohn) |
| UM66T11 L/S | Love Me Tender, Love Me True |
| UM66T13 L/S | Easter Parade |
| UM66T19 L/S | For Elise |
| UM66T32 L/S | Waltz |
| UM66T33 L/S | Mary Had a Little Lamb |
| UM66T34 L/S | The Train is Running Fast |
| UM66T68 L/S | It's a Small world |

Figure 5:
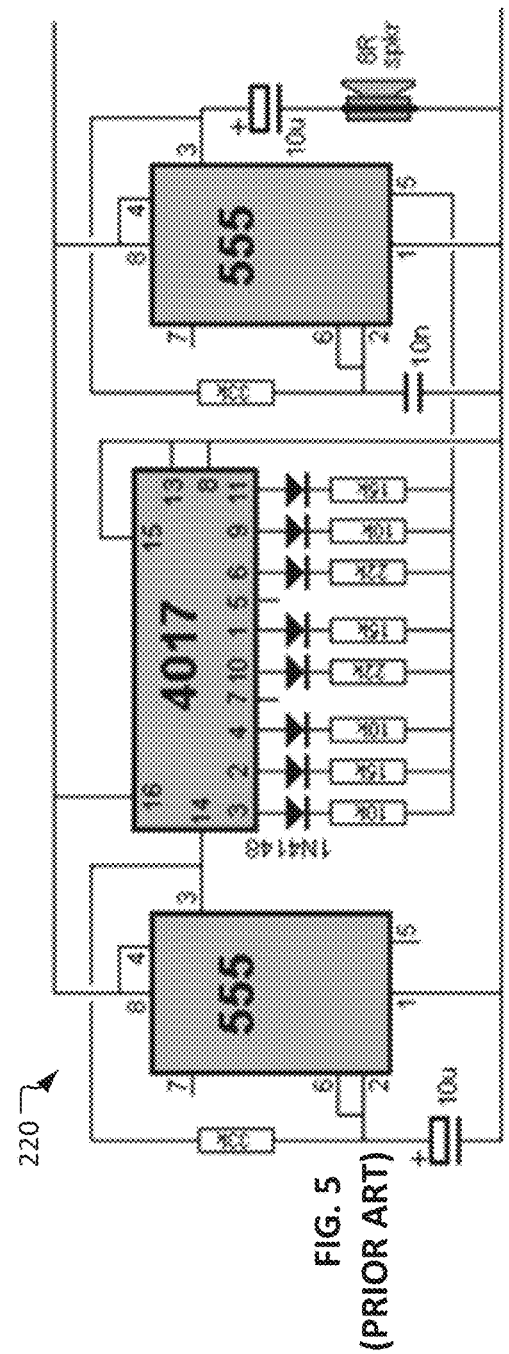
FIG. 5 shows a typical prior art timer delay unit circuitry that includes 555 timer ICs and a 4017 decade counter IC.

Typical timer delay unit 220 circuitry that may be part of the processing unit 202 is shown in FIG. 5 to include 555 timer ICs and a 4017 decade counter IC. This circuitry may be used to generate a start/shutoff tone and timing, and the delay signal timing between the rhythm producer 230 and the injection module 240 via the microprocessor 210 in the processing unit 202. The power supply 250 generates the operating voltages providing power for these integrated circuits and the necessary polarization currents for the electromagnets, which will be described below.

Figure 6:
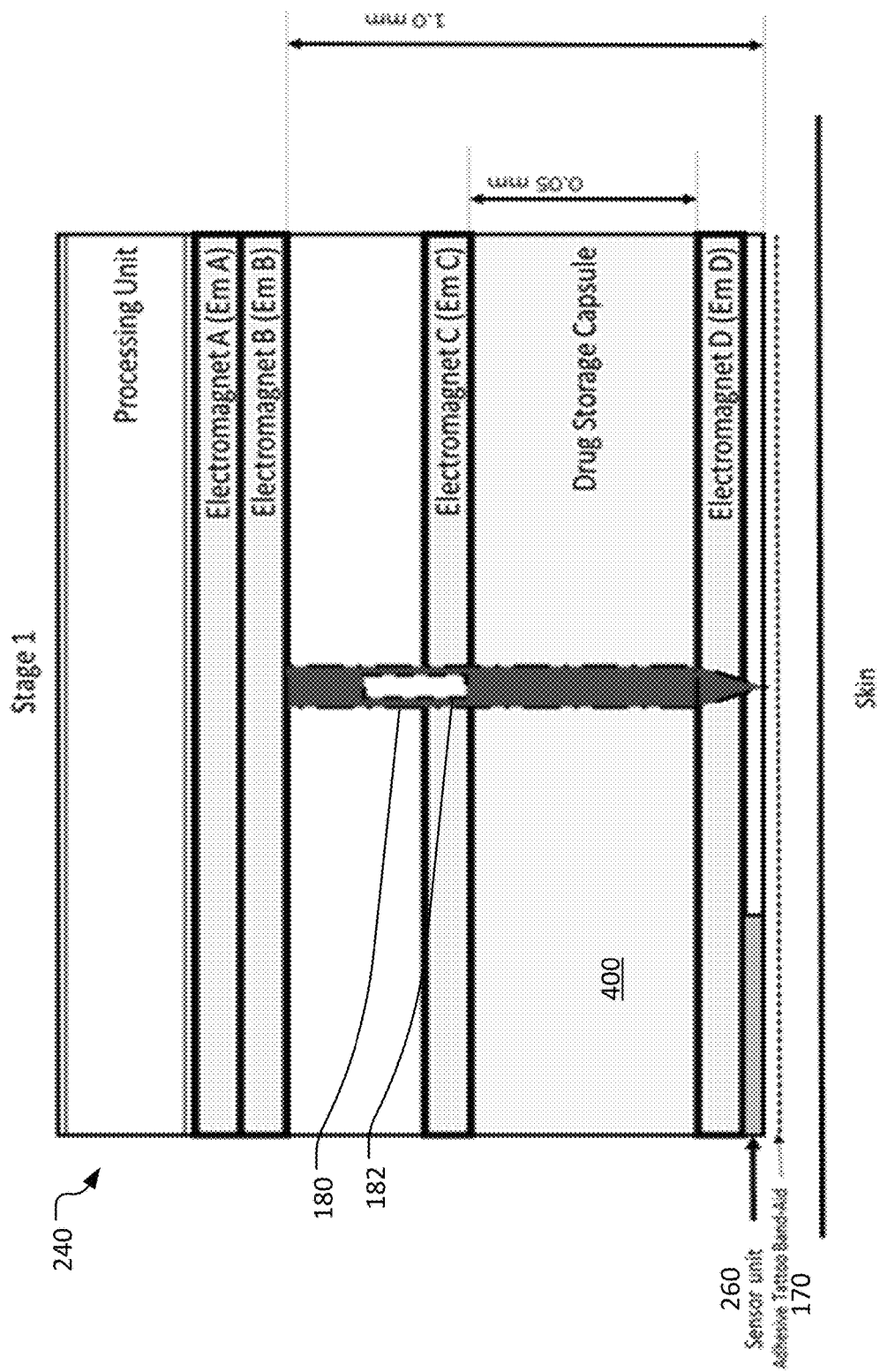
FIG. 6 schematically shows an injection module of a vaccination unit having electromagnets and Stage 1 of a vaccination process in accordance with an embodiment of the invention.

FIG. 6 schematically shows an injection module 240 in accordance with an embodiment of the invention. The injection module 240 is a hermetically sealed and sterilized module that includes four electromagnets (Em A, Em B, Em C, and Em D), a slotted microneedle 180, and a drug storage capsule 400 or fluid-containing chamber. In other embodiments, an array of microneedles 180 are used instead of a single slotted needle 180. The array of microneedles 180 may be of the type described above for the Emory and Georgia Institute of Technology research for medicine/drug delivery or the like, as discussed. The electromagnets Em A, Em B, Em C, and Em D are oval shaped in this embodiment although other shapes are contemplated, such as circular. These electromagnets include wire or other conductive material windings as is typical for electromagnets, and become activated once electrical currents from the power source flow through these conductors to produce a magnetic field with a magnetic polarity in a direction for each electromagnet depending on the direction of current flow, as would be understood by a person of ordinary skill in the art.

The processing unit 202 controls activation of the injection module 240 as will be described further below. Electromagnets Em A and Em D are fixed electromagnets, that is, they are held in a fixed position inside the vaccination unit 120. They magnetically repel or attract in respect to their magnetic polarities. Electromagnets Em B and Em C on the other hand are moveable electromagnets as in a vertical (i.e., top to bottom) direction of the page of FIG. 6 that also magnetically repel or attract in respect to magnetic polarity. The electromagnets Em B, Em C, and Em D have an opening, e.g., a center hole, that allows for the microneedle 180 to advance and later retract to provide the vaccination as described further below. In some embodiments, the microneedle 180 is slotted to allow the medicine/drug fluid or material to enter the needle 180 for the injection process also as described below.

In this embodiment, preferably the needle 180 is 1.0 mm long or approximately 1.0 mm (e.g., ±10%) long, with an 18-gauge diameter, and is fixedly attached to Em B, for example, using a plastic, insulating, or a nonconductive support or support structure. The conductor of Em B may be wound around this support or support structure, and the conductors of the other Ems described herein may also be wound around similar supports or support structures. Other sized needles 180 are also contemplated, for example, 23 gauge, or gauges between 18 and 23, depending on the requirements for giving the vaccine, the vaccine material, the amount of dosage needed, and the age and physical characteristics of the patient. Once the bracelet 100 is activated, after the described delay and while the patient may be distracted or entertained by the audible sounds, the needle 180 is advanced into the patient's dermis layer of the skin to inject the vaccine and later be retracted.

As described above, in accordance with an embodiment of the invention, the bracelet 100 is affixed to the patient's limb and activated by pushing the "Press Me" button 140, which in turn activates electrical or electronic signals to the processing unit 202. Other activation mechanisms involving a switch, haptic like a touchscreen, etc. or the like instead of a physical button 140 are contemplated in other embodiments to generate these electrical or electronic signals. The electrical or electronic signals are received by the microprocessor 210 in the processing unit 202, which triggers the rhythm producer 230 and the timer delay unit 220. An activation tone is played and the audible sounds chosen by the patient or automatically chosen by the vaccination platform 100 start playing through the speaker(s) 150 to distract or entertain the patient for the duration of the vaccination process (e.g., a duration of 60 seconds). The timer delay unit 220 counts or a timer times a period of time (e.g., 10 seconds) using the circuitry shown in FIG. 5, for example. Once the 10 seconds are reached or counted, if the microprocessor 210 then detects a skin sensing control signal from the LDR 260 because the vaccination unit 120 is properly affixed to the patient's skin, the microprocessor 210 triggers the electromagnets Em A, Em B, Em C, and Em D, as follows.

The initial (stage 1 as depicted in FIG. 6) electromagnet polarity states are shown in Table B.

TABLE B

| Stage 1 Electromagnet States | |
|---|---|
| Electromagnet (Em) | Polarity |
| A | North |
| B | South |
| C | South |
| D | South |

In Stage 1, the microneedle(s) 180 is in its safety position and not moving, and the slot 182 in the needle 180 is not filing with the medicine/drug as the slot 182 is not yet located inside the drug delivery capsule 400.

Figure 7:
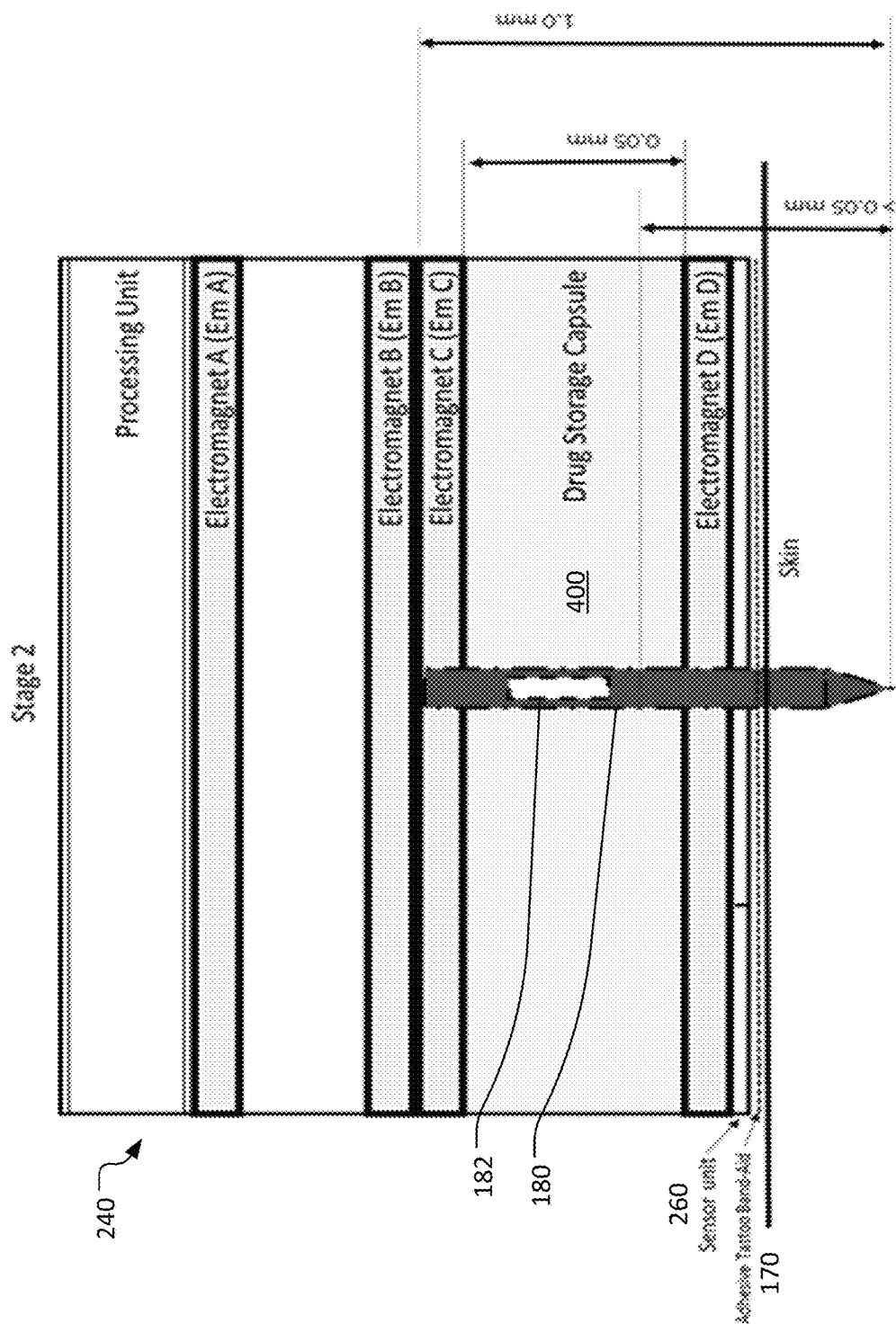
FIG. 7 schematically shows the injection module and electromagnets of FIG. 6 and Stage 2 of the vaccination process in accordance with an embodiment of the invention.

FIG. 7 shows Stage 2 of the vaccination process and the electromagnet polarity states in Stage 2 are shown in Table C. Upon skin contact and detection by the microprocessor 210 of the skin sensing signal from the LDR 260, the microprocessor 210 sends the control signal to change the polarity of Em A to South, Em C to North and Em D to North. This polarity change causes Em B to be attracted and move to Em C, and because Em B is physically coupled to the microneedle's 180 plastic, insulating or nonconductive support (e.g., its windings are wound around the same structure), the microneedle 180 is advanced from its safety position within the VAC-I-BRACE' 100 and the needle 180 tip enters into the patient's skin as Em B and Em C move together toward Em D as described below.

TABLE C

| Stage 2 Electromagnet State | |
|---|---|
| Electromagnet (Em) | Polarity |
| A | South |
| B | South |
| C | North |
| D | North |

As Em B and Em C move together toward Em D, the slot 182 in the microneedle 180 enters the drug capsule 400 or reservoir and the medicine/drug fills the orifice within the microneedle 180 through the slot 182 for delivering the medicine/drug in the injection. The initial skin piercing is approximately to a depth of 0.05 mm (e.g., 0.05±10% mm). As the microneedle 180 advances into the patient's skin and begins to inject the medicine/drug as the electromagnets Em B and Em C move, the drug capsule 400 or reservoir also begins to collapse and its volume is reduced by compression (e.g., the same needle support structure may apply the compressive force). This facilitates the flow of the medicine/drug into and through the microneedle 180.

FIG. 8 shows Stage 3 of the electromagnets Em A, Em B, Em C, and Em D and the vaccination process. The electromagnet polarity states in Stage 3 are shown in Table D. When Em B is attracted to Em C, the two form an electromagnet union Em U and the microprocessor 210 sets the polarity of this union Em U to North by control of the directions of current flow in the Em B and Em C. Simultaneously the polarity of the Em D changes to south, which attracts the Em U and results in its motion towards Em D, thereby pushing the microneedle(s) 180 further into the patient's skin and releasing the final dosage of the medicine/drug. The injection fluid material is forced through the slot 182 and through the microneedle's 180 hollow interior orifice into the patient's dermis as the support structure physically holding and providing mechanical stability to the Em B and Em C and the needle 180 applies the downward force on the drug storage capsule 400, reducing its volume. The fluid has no place to go except into the patient's skin because the drug storage capsule 400 remains otherwise sealed by this support structure as it moves down with the needle 180. The slot 182 in the microneedle 180 may move below the drug storage capsule 400 when the latter is collapsed, or in other embodiments, the slot 182 may still be located within the collapsed drug storage capsule 400. For safety, as the needle 180 moves and the capsule 400 collapses, the polarity of Em A is then changed to North, which further helps in repulsion of Em U from Em A as Em U proceeds towards Em D.

TABLE D

| Stage 3 Electromagnet State | | |
|---|---|---|
| Electromagnet (Em) | | Polarity |
| A | | North |
| U | B | North |
| | C | |
| D | | South |

Figure 9:
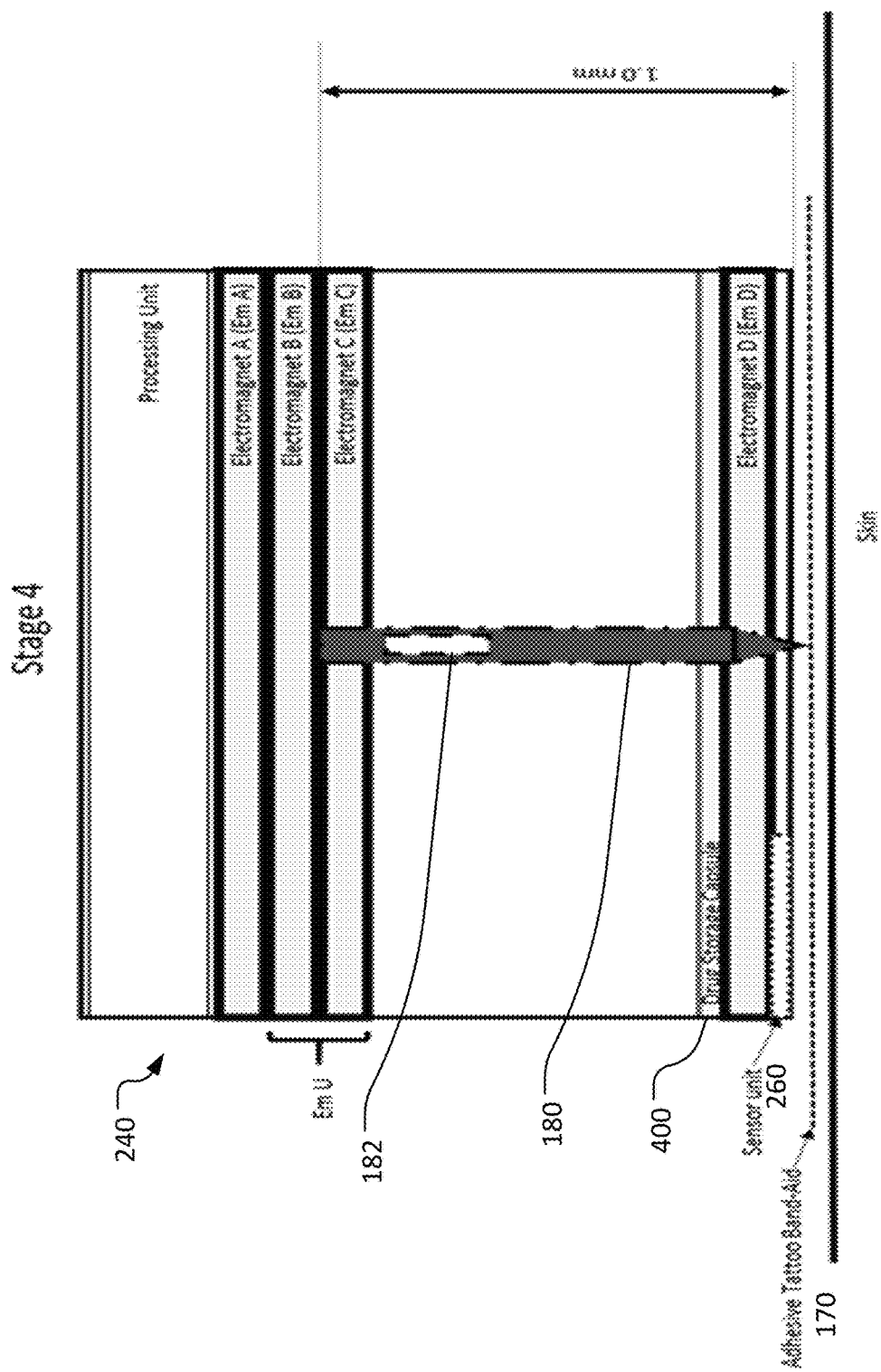
FIG. 9 schematically shows the injection module and electromagnets of FIG. 6 and Stage 4 of the vaccination process in accordance with an embodiment of the invention.

FIG. 9 shows Stage 4 of the electromagnets and the vaccination process. The electromagnet polarity states in Stage 4 are shown in Table E. When the microprocessor 210 receives an electrical or electronic signal indicating or sensing the attraction and motion of Em U to its furthest extent towards Em D, and the drug delivery capsule 400 is collapsed, the microprocessor 210 changes the polarity of the Em D to North and Em A to South, thereby causing repulsion of the Em U from Em D and its attraction to Em A. As a result, the Em U moves upwards towards the Em A, which causes the microneedle 180 to recede from the patient's skin into the safety position of FIG. 6. The drug storage capsule 400 remains collapsed, however.

TABLE E

| Stage 4 Electromagnet State | | |
|---|---|---|
| Electromagnet (Em) | | Polarity |
| A | | South |
| U | B | North |
| | C | |
| D | | North |

At this point, which occurs preferably within approximately 45 seconds (e.g., 45±10% seconds) since the vaccination unit 120 was initialized, the drug or medicine dose has been completely injected into the patient and the microneedle 180 has been retracted back into the vaccination unit 120 safety position. The audible sounds continue to play for approximately 60 seconds (e.g., 60±10% seconds). Other timings are contemplated in other embodiments of the invention, for example, injection and retraction may occur in greater than and inclusive of 20 seconds after vaccination unit 120 initialization and the audible sounds continue to play for less than and inclusive of 90 seconds or less than and inclusive of 1.5 minutes. The amount of these times may be determined by the age or other characteristics of the patient. When the timer delay count or timer reaches the end of the audible sounds (e.g., counts to 60 seconds or the tune or song ends), the microprocessor 210 is deactivated (e.g., voltage or power is cut off), indicating that the entire drug delivery process is completed. The bracelet 100 then may be removed from the patient. The typical vaccination dosage for most vaccines is in the range of 0.5 ml to 1 ml inclusive (or approximately that range, e.g., ±10%) subcutaneously. Table 2 from immunize.org (reviewed by the CDC) shows typical dosages (www.immunize.org/catg.d/p3085.pdf). The VAC-I-BRACEυ 100 is designed to deliver such dosages in accordance with embodiments of the invention.

The volume of the drug delivery capsule 400 should accommodate the 0.5-1.0 ml or approximately these volumes inclusive (e.g., within ±10%) of medicine/drug for a typical vaccine. Most children's vaccines are typically 0.5 ml unless they are adolescents, in which case a higher dosage range, like that for adults, is contemplated. If the drug delivery capsule 400 is assumed to be a cylinder and the desired volume V is 0.5 ml, the radius R of the cylinder for a height H of 0.05 mm may be calculated, for example, as follows:

$$V = \pi R^2 H = (3.14) R^2 H$$

So, 0.5 ml=(3.14)$R^2$(0.05 mm) and R=Sqrt((0.5)/((3.14)(0.05))) mm

Therefore, R=1.78 mm or approximately 1.8 mm.

Similarly, if the volume V of the medicine/drug delivered needs to be 1.0 ml, R=2.52 mm or approximately 2.5 mm. Thus, in accordance with embodiments of the invention, the radius of the capsule 400 can vary from approximately 1.5 to 2.5 mm inclusive (within e.g., ±10%), for a height of 0.05 mm to accommodate the vaccination volume of 0.5 to 1.0 ml inclusive. The height and the radius may be varied to accommodate other required dosages outside this range in accordance with other embodiments of the invention, and other dimensions could be used for other shapes of the drug delivery capsule to accommodate the desired dosages, as would be understood by a person of ordinary skill in the art.

TABLE 2

Typical Dosages

| Vaccine | Dose | Route |
|---|---|---|
| Diptheria, Tetanus, Pertussis (DTaP, DT, Tdap, Td) | 0.5 ml | IM |
| *Haemophilus influence* type b (Hib) | 0.5 mL | IM |
| Hepatitis A (HepA) | ≤18yrs: 0.5 mL<br>≥19 yrs: 1.0 mL | IM |
| Hepatitis B (HepB)<br>Persons 11-15 yrs may be given Recombirax HB (Merck) 1.0 mL adult formulation on a 2-dose schedule. | ≤19 yrs: 0.5 mL<br>≥20 yrs: 1.0 mL | IM |
| Human papillomavirus (HPV) | 0.05 mL | IM |
| Influenza, live attenuated (LAIV) | 0.2 mL<br>(0.1 mL in each nostril) | Intranasal spray |
| Influenza, inactivated (IIV); recombinant (RIV), for ages 18 years and older | 6-35 mos: 0.25 mL<br>3 yrs: 0.5 mL | IM |
| Influenza (IIV) Fluzone Intradermal, for ages 18 thru 64 years | 0.1 mL | ID |
| Measles, Mumps, Rubella (MMR) | 0.5 mL | Subcut |
| Meningococcal conjugate (MCV4 [MenACWY]) | 0.5 mL | IM |
| Meningococcal serogroup B (MenB) | 0.5 mL | IM |
| Meningococcal polysaccharide (MPSV) | 0.5 mL | Subcut |
| Pneumococcal conjugate (PCV) | 0.5 mL | IM |
| Pneumococcal polysaccharide (PPSV) | 0.5 mL | IM or Subcut |
| Polio, inactivated (IPV) | 0.5 mL | IM or Subcut |
| Rotavirus (RV) | Rotarix: 1.0 mL<br>Rotateq: 2.0 mL | Oral |
| Varicella (Var) | 0.5 mL | Subcut |
| Zoster (Zos) | 0.65 mL | Subcut |
| Combination Vaccines | | |
| DTap-HepB-IPV (Pediarix)<br>DTaP-IPV/Hib (Pentacel)<br>DTaP-IPV (Kinrix; Quadracel)<br>Hib-HepB (Comvax)<br>Hib-MenCY (MenHibrix) | 0.5 mL | IM |
| MMRV (ProQuad) | ≤12 yrs: 0.5 mL | Subcut |
| HepA-HepB (Twinrix) | ≥18 yrs: 1.0 mL | IM |

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A device for administering a vaccine intradermally, comprising:
   a bracelet including a fastener for attaching the bracelet to a patient's appendage;

a vaccination unit attached to the bracelet, the vaccination unit including:
a microneedle;
a set of electromagnets including a first electromagnet that is fixedly attached to the microneedle and a second electromagnet; and
a collapsible drug storage capsule disposed between the first and second electromagnets, wherein the first electromagnet is movable in relation to the second electromagnet to thereby cause a compression of the collapsible drug storage capsule that causes the vaccine in the collapsible drug storage capsule to eject from the microneedle;
an audio unit attached to the bracelet and including at least one microspeaker; and
a button attached to the bracelet for activating electrical signals to play an audible sound through the at least one microspeaker, and after a delay, to change relative polarity states of the set of electromagnets to cause the first electromagnet to move the microneedle to: (i) pierce skin of the patient and (ii) administer the vaccine intradermally to the patient through the microneedle.

2. The device of claim 1, wherein the delay is one minute or less.

3. The device of claim 2, wherein the delay is fifteen seconds or less.

4. The device of claim 1, wherein the vaccine delivers a medically effective dose through the microneedle.

5. The device of claim 1, further comprising an adhesive sterilized bandage or a gauze removably affixed to the bracelet for application to the patient's appendage on or over an area of penetration of the microneedle into the patient's skin.

6. The device of claim 1, wherein the bracelet comprises a non-allergic bracelet.

7. The device of claim 1, further comprising third and fourth electromagnets.

8. The device of claim 1, wherein the bracelet is configured to be secured to the patient's appendage by adhesives and an adjustable bracelet lock attached to the bracelet.

9. The device of claim 1, wherein the bracelet has one or more colors or graphic designs.

10. The device of claim 1, wherein the audible sound comprises one or more of musical tones, tunes, and songs.

11. The device of claim 1, wherein the device reduces a likelihood of needle stick injury.

12. The device of claim 1, wherein the device promotes patient compliance for receiving vaccines.

13. A vaccination platform for distracting a patient prior to medicine or drug delivery, comprising:
a bracelet for attachment to the patient's appendage;
a vaccination unit located in a center portion of the bracelet, the vaccination unit comprising:
a processing unit;
a rhythm producer for producing audible sounds; and
an injection module including a first electromagnet, a second electromagnet, a microneedle, and a collapsible drug delivery capsule disposed between the first and second electromagnets, the microneedle affixed to the first electromagnet and having a proximal end communicating with the collapsible drug delivery capsule and a distal end to provide an intradermal vaccination to the patient, wherein the first electromagnet is movable in relation to the second electromagnet to thereby cause a compression of the collapsible drug delivery capsule that causes a vaccine in the collapsible drug delivery capsule to eject from the microneedle when relative polarity states of the first and second electromagnets are changed by the processing unit, wherein the processing unit controls a delay between a start of the audible sounds and when the vaccination occurs; and
a non-allergic adhesive located on the bracelet to secure the bracelet to the patient's skin.

14. The vaccination platform of claim 13, wherein the bracelet further comprises a light configured to flash to indicate when the vaccination may occur.

15. The vaccination platform of claim 13, wherein the microneedle is a first microneedle, and further comprising one or more additional microneedles.

16. The vaccination platform of claim 13, further comprising third and fourth electromagnets.

17. The vaccination platform of claim 13, further comprising an adhesive sterilized bandage or a gauze removably affixed to the bracelet for application to the patient's appendage on or over an area of penetration of the microneedle into the patient's skin.

* * * * *